United States Patent
Ortner et al.

(10) Patent No.: US 12,178,679 B2
(45) Date of Patent: Dec. 31, 2024

(54) DENTAL ARTICLE WITH A COATING COMPRISING NANOSTRUCTURES MADE OF YTTRIA-STABILIZED ZIRCONIA

(71) Applicants: STRAUMANN HOLDING AG, Basel (CH); FRAUNHOFER GESELLSCHAFT ZUR FÖRDERUNG DER ANGEWANDTEN FORSCHUNG E.V., Munich (DE)

(72) Inventors: Kai Thomas Ortner, Braunschweig (DE); Marc Stephan, Basel (CH)

(73) Assignees: STRAUMANN HOLDING AG, Basel (CH); FRAUNHOFER GESELLSCHAFT ZUR FÖRDERUNG DER ANGEWANDTEN FORSCHUNG E.V., Munich (DE)

(*) Notice: Subject to any disclaimer, the term of this patent is extended or adjusted under 35 U.S.C. 154(b) by 716 days.

(21) Appl. No.: 17/262,849

(22) PCT Filed: Jul. 23, 2019

(86) PCT No.: PCT/EP2019/069799
§ 371 (c)(1),
(2) Date: Jan. 25, 2021

(87) PCT Pub. No.: WO2020/020887
PCT Pub. Date: Jan. 30, 2020

(65) Prior Publication Data
US 2021/0236246 A1   Aug. 5, 2021

(30) Foreign Application Priority Data
Jul. 24, 2018   (EP) .................................. 18185122

(51) Int. Cl.
*A61C 8/00*   (2006.01)
*C23C 14/08*   (2006.01)
*C23C 14/34*   (2006.01)

(52) U.S. Cl.
CPC .......... *A61C 8/0015* (2013.01); *C23C 14/088* (2013.01); *C23C 14/34* (2013.01); *A61C 2201/00* (2013.01)

(58) Field of Classification Search
CPC . A61C 8/0015; A61C 2201/00; C23C 14/088; C23C 14/34
See application file for complete search history.

(56) References Cited

U.S. PATENT DOCUMENTS

| 5,242,299 A * | 9/1993 | Yoshida .................. A61C 7/12 433/10 |
| 6,586,115 B2 | 7/2003 | Rigney et al. |

(Continued)

FOREIGN PATENT DOCUMENTS

| CN | 104661615 A | 5/2015 |
| CN | 105420662 A | 3/2016 |

(Continued)

OTHER PUBLICATIONS

Oct. 16, 2019 International Search Report issued in International Patent Application No. PCT/EP2019/069799.

(Continued)

*Primary Examiner* — Nicholas D Lucchesi
(74) *Attorney, Agent, or Firm* — Oliff PLC (57) ABSTRACT

A dental article including a dental article body made of a ceramic material and a coating formed on the surface of said dental article body. The coating includes crystalline nanostructures made of yttria-stabilized zirconia $YSZ_1$, the crys- (Continued)

tal habitus of at least a portion of the nanostructures having at least approximately the shape of a regular convex polyhedron.

19 Claims, 3 Drawing Sheets

(56) References Cited

U.S. PATENT DOCUMENTS

| | | | | |
|---|---|---|---|---|
| 8,298,329 | B2* | 10/2012 | Knapp | C04B 35/486 106/35 |
| 2012/0156472 | A1* | 6/2012 | Brannvall | A61K 6/818 427/2.29 |
| 2013/0157225 | A1* | 6/2013 | Morris | A61K 6/842 433/199.1 |
| 2013/0171589 | A1* | 7/2013 | Velamakanni | A61C 5/77 427/2.27 |
| 2017/0100309 | A1* | 4/2017 | Morris | A61C 7/282 |

FOREIGN PATENT DOCUMENTS

| | | |
|---|---|---|
| EP | 0 388 576 A1 | 9/1990 |
| EP | 1 982 670 A1 | 10/2008 |
| EP | 2 263 991 A1 | 12/2010 |
| EP | 2 367 196 A1 | 9/2011 |
| WO | 2006/102347 A2 | 9/2006 |
| WO | 2012/030565 A1 | 3/2012 |
| WO | 2013/056844 A1 | 4/2013 |
| WO | 2014/195025 A2 | 12/2014 |

OTHER PUBLICATIONS

Erica C. Teixeira et al. "Effect of YSZ Thin Film Coating Thickness on the Strength of a Ceramic Substrate," Wiley InterScience, 2007, pp. 459-463.

Jan. 26, 2021 International Preliminary Report on Patentability issued in International Patent Application No. PCT/EP2019/069799.

* cited by examiner

DENTAL ARTICLE WITH A COATING COMPRISING NANOSTRUCTURES MADE OF YTTRIA-STABILIZED ZIRCONIA

The present invention relates to a dental article according to the preamble of claim 1, to a process for providing a dental article and to the use of the dental article as a dental implant.

Dental implants are well known in the art. Generally, they comprise an anchoring part intended to be anchored in a patient's jaw bone and a head part intended to form the basis on which a suprastructure, such as a bridge or crown, is mounted. The mounting of the suprastructure is thereby often performed by using an intermediate, i.e. a so-called "abutment" (also referred to as "secondary part"), as it is the case in a "two-part implant system" or "multi-part implant system".

Currently used dental implants are often made of titanium, which apart from being biocompatible exhibits a high mechanical strength.

In aiming at an aesthetically pleasing colour of the implant material, and in particular a colour fitting into the natural environment into which the dental implant is to be placed, the use of ceramics has been proposed. Among these, zirconia ceramics have turned out to be very well suited due to their mechanical strength and biocompatibility. Specifically, yttria-stabilized tetragonal zirconia has been proven to be the material of choice.

Besides the above requirements of exhibiting high mechanical strength and biocompatibility, successful implantation requires that the dental implant is designed in a manner in which it is accepted by the human body. When detected as a foreign object and rejected by the immune system, the dental implant may cause inflammation, which not only causes pain to the patient but often also leads to the necessity of follow-up surgery to replace or remove the implant.

Acceptance of the human body towards the dental implant is to an important degree determined by the implant's surface. Thus, the implant's surface must be engineered in a manner that cells attach to it and that natural body tissue, specifically bone tissue or soft tissue, starts growing around it, thus avoiding rejection of the dental implant by the human body.

In particular, it is required that a direct structural and functional connection between living jawbone and the implant surface is achieved shortly after implantation. This is referred to in the art as "osseointegration" which stands for the implant's tendency to safely ossify within a short healing time so that a permanent bond between implant and bone is obtained.

The interaction between the surface of the implant and the body fluid as well as the surrounding bone tissue is governed by proteins which adhere, i.e. adsorb, to the surface once the implant gets in contact with blood, and in particular by the fibrin network formed on the implant surface. It is assumed that the proteins adsorbed on the implant surface, particularly the fibrin network formed, influence(s) the cellular behaviour, e.g. the differentiation and mineralization, of the bone cells. In order to achieve a fast and strong interaction between the implant and bone tissue, protein adherence, and in particular fibrin network formation, on the surface is thus of paramount importance.

One important factor that influences protein adherence is the hydrophilicity of the surface as well as its surface topography.

For titanium implants, a breakthrough technology in providing an osseointegrative surface is described in EP-A-0 388 576 relating to a treatment combining sandblasting the surface (for providing a macroscopic topography or "macroroughness") and subsequent etching with a reducing acid (for providing a microscopic topography or "microroughness" superimposing the "macroroughness"). By this treatment, a so-called SLA® surface with exceptionally good osseointegrative properties is achieved.

In order to provide an osseointegrative surface topography on a dental implant made of a ceramic material, EP-A-1 982 670 suggests a treatment, whereby at least a part of the surface of the dental implant is etched with an etching solution comprising hydrofluoric acid at a temperature of at least 70° C., thereby removing discrete grains or agglomerates of from grains the ceramic material.

Apart from the importance of the surface having a macroscopic and microscopic topography, it has recently been found that also the presence of specific nanostructures—i.e. structures in the sub-micron range-plays an important role in the adherence of proteins and ultimately in a good bone or soft tissue interaction with the implant.

In this regard, WO 2013/056844 describes a process for providing structures for improved protein adherence on the surface of a body, specifically an implant. The process comprises the step of storing an acid-etched basic body in an aqueous solution, by which nanostructures are formed on the surface of the basic body.

Also, WO 2014/195025 deals with the formation of nanostructures on a dental implant, but for a different purpose, namely for obtaining a strong interaction between a dental implant and the surrounding soft tissue. In this regard, WO 2014/195025 suggests a surface topography, which is smooth when regarded in macroscopic and microscopic scale, but nevertheless provides a nanoscopic structure due to the presence of nanostructures.

Whereas suitable storing conditions lead to the formation of nanostructures on titanium, no nanostructures are formed on zirconia ceramics.

In addition, it has been found that when performing an etching treatment according to the technology described in EP-A-1 982 670, yttria-stabilized zirconia can suffer a depletion in yttrium, which both can have a negative impact on the strength as on the hydrothermal stability of the material.

Although yttrium depletion can be limited to a certain extent by restricting the etching period, it cannot be completely avoided. In addition, restricting the etching period necessitates that etching is carried out at a relatively high temperature. Given the fact that hydrofluoric acid used for the etching according to EP-A-1 982 670 is highly toxic, particularly strict safety measures have to be taken for etching at high temperature.

In consideration of the drawbacks mentioned above, the problem of the present invention is thus to provide a dental article made of a ceramic material having a high strength and a high hydrothermal stability, the surface of which allowing for a relatively fast and strong interaction with the surrounding tissue.

According to a specific aspect, fast a and strong interaction with the surrounding tissue shall be achieved in a manner, by which the strength and the hydrothermal stability of the material is at least essentially maintained. The problem is solved by the subject matter of claim 1 and by the process of claim 13. Preferred embodiments are defined in the dependent claims.

According to claim 1, the present invention thus relates to a dental article comprising a dental article body made of a ceramic material and a coating formed on the surface of said dental article body. As further defined in claim 1, the coating comprises crystalline nanostructures made of yttria-stabilized zirconia $YSZ_1$, the crystal habitus of at least a portion of the nanostructures having at least approximately the shape of a regular convex polyhedron.

By the presence of the nanostructures defined in claim 1, a surface of improved biological activity can be achieved, as will be discussed in the context of the specific working examples. This is of particular relevance in view of the body being used as a dental implant, for which a good interaction with the surrounding tissue is of high importance for ensuring a successful implantation.

The improved biological activity of the surface is at least partially owed to the nanostructures, which allow for an improved interaction of the dental article with the surrounding tissue.

In this regard, the formation of the nanostructures has been found to go along with an enhanced mineralisation of bone tissue surrounding the body.

Specifically, the nanostructures form nanoscopic peaks projecting outward from the body's surface. Without wanting to be bound by the theory, it is postulated that cell membrane proteins can directly or indirectly, i.e. by mediation of other proteins, adhere to the nanostructures and, thus, establish an anchorage of the cells to the implant surface. In view of the endosseous portion of the implant, this ultimately allows the surrounding bone tissue to strongly interact with the surface, e.g. by migration of osteoblasts into the pits or pores given by the specific topography.

As the case may be, the nanostructures forming retention sites not only allow for an optimal bone tissue interaction and, thus, a good osseointegration, they also allow for an optimal soft tissue interaction and thus an effective seal between the implant's endosseous portion and the oral environment to be achieved.

The term "coating" as used in the context of the present invention encompasses both a continuous coating, as well as a discontinuous coating. According to a particular embodiment of the present invention, the coating is continuous and at least partially seals the surface or the part of the surface on which it is applied.

Between the coating and the dental article body, on which it is formed, the dental article of the present invention exhibits a discrete interface. It is therefore in clear distinction to a ceramic body in which an additional component, such as additional yttrium, is s incorporated into the ceramic material without forming a discrete interface, as it is the case in ceramic bodies in which the additional component is incorporated by heat-induced diffusion.

Generally, the nanostructures are conjoined with the surface of the dental article body, meaning that they are intrinsically linked to the surface and, thus, bonded firmly enough not to be abraded easily during use, in particular during insertion into bone.

As mentioned, at least a portion of the nanostructures according to the present invention have a crystal habitus, which has at least approximately the shape of a regular polyhedron. Specifically, the crystal habitus has at least approximately the shape of a convex regular polyhedron encompassing the following (defined by their Schläfli symbol): a tetrahedron {3, 3}, a cube {4, 3}, an octahedron {3, 4}, a dodecahedron {5, a 3} and/or icosahedron {3, 5}

By the term "at least approximately the shape of a regular polyhedron" any crystal habitus is encompassed, the shape of which slightly deviates from a perfect polyhedron. In particular, a crystal habit having the form of a distorted or contorted polyhedron is also encompassed by the definition of the present invention. Still further, any crystal habitus having the shape of two or more polyhedrons penetrating each other is encompassed.

Specifically, the term "approximately the shape of a regular convex polyhedron" relates to a deviation from the mathematical parameters, such as angles, areas etc. of the respective perfect polyhedron.

More specifically, the definition of the crystal habitus of the nanostructures by the term "having at least approximately the shape of a regular convex polyhedron" encompasses nanostructures, which on their side facing away from the surface, i.e. the distal side, have the shape of the respective sector of a regular convex polyhedron or slightly deviates therefrom, but which on the side facing the surface, i.e. the proximal side, are distorted.

A specifically high biological activity and, hence, a particularly good interaction with the surrounding tissue has been determined for embodiments, in which the nanostructures' crystal habitus has at least approximately the shape of a tetrahedron or an octahedron.

According to a particular embodiment of the present invention, the nanostructures have on their distal side the shape of the respective sector of a regular convex polyhedron, specifically of a tetrahedron or an octahedron, or slightly deviates therefrom, and which on their proximal side, are distorted. More particularly, the nanostructures are on their proximal side of a columnar shape forming a surface oriented tilted columnar structure, which is a result of the nanostructures being conjoined with the surface of the dental article body.

According to a further aspect, the present invention thus also relates to a dental article comprising a dental article body made of a ceramic material and a coating formed on the surface of said dental article body, wherein the coating comprises crystalline nanostructures made of yttria-stabilized zirconia $YSZ_1$, at least a part of the nanostructures comprising a proximal region protruding from the surface and being of a columnar shape, said proximal region passing into a distal region of the nanostructure, said distal region having a mean diameter wider than the one of the proximal region. Specifically, the distal region has the shape of the respective sector of a regular convex polyhedron or slightly deviates therefrom, as mentioned above.

According to a particular embodiment, the proximal region has a length ranging from about 1 nm to about 250 nm, specifically from about 20 nm to about 100 nm, and more specifically from about 30 nm to about 60 nm. Typically, the proximal region or a portion thereof is at least approximately cylindrical or conical.

According to a further particular embodiment, the distal region extends in the longitudinal direction (i.e. the direction defined by the longitudinal axis of the proximal region) from about 2 nm to about 80 nm, specifically from about 5 nm to about 40 nm, and more specifically from about 10 nm to about 20 nm.

Irrespective of the improved biological activity obtained by the present invention, the surface of the dental article is inert in the sense that even after prolonged implantation, it remains constant over time. Specifically, there is no phase transition phenomena that might otherwise occur in ceramic material during processing and exposure in the oral environment, and the structure of the material presented to the surrounding tissue does not undergo any changes which might negatively affect the interaction between the cells and the implant's surface. This is of high relevance for a successive implantation, since the interaction between implant and bone tissue/soft tissue is very sensitive and a safe ossification of the implant is only established after several weeks.

By applying a coating of yttria-stabilized zirconia, the present invention further allows to mitigate issues that might arise due to a depletion of yttrium. This can be of relevance for dental articles that are subjected to a pre-treatment for providing a macroscopic and/or a microscopic topography, in particular to an etching treatment according to the technology described in EP-A-1 982 670.

In addition, also the hydrothermal stability of the material can at least to a certain degree be maintained by the present invention. In comparison to an article suffering yttrium depletion, hydrothermal aging phenomena of the dental article, caused by moisture-induced change in the material structure, can thus be decreased.

According to a preferred embodiment of the present invention, the amount of yttria in the yttria-stabilized zirconia $YSZ_1$ is higher than 3 mol-%. This allows an yttria-stabilized zirconia of preferred crystallographic structure and crystal habitus to be achieved.

According to a further preferred embodiment, the amount of yttria in the yttria-stabilized zirconia $YSZ_1$ is lower than 12 mol-%.

According to a particularly preferred embodiment, the amount of yttria in the yttria-stabilized zirconia $YSZ_1$ is in a range from 6 to 8 mol-%, allowing for providing a cubic or cubic-like phase stable at room temperature, and in particular an intermediate phase between a tetragonal and a cubic phase.

As mentioned above, the dental article body is typically made of zirconia, preferably of yttria-stabilized zirconia $YSZ_2$. In this regard, it is particularly preferred that the percentage of yttrium in the yttria-stabilized zirconia $YSZ_1$ differs from the percentage of yttrium in the yttria-stabilized zirconia $YSZ_2$. In other words, the yttrium-content in the coating is different from the yttrium-content in the dental article body. As, according to a further preferred embodiment, the dental article body is made of 3 mol % yttria stabilized tetragonal zirconia, the yttrium content of the coating is preferably higher than the one of the dental article body.

In providing a coating comprising yttria-stabilized zirconia nanostructures, and in particular zirconia of an increased yttrium content, the present invention is diametrically different to what is thought in EP-A-2 046 235 relating to a dental implant, the surface of which having a depletion region with a reduced content of yttrium oxide or aluminium oxide as compared with the inner volume. By providing a dental article comprising a coating of the crystalline nanostructures defined in claim 1, the present invention rather avoids an yttrium depletion zone to occur in the dental article body and, thus, provides a dental article having improved strength and hydrothermal stability compared to a body made of YSZ suffering from yttrium depletion, as mentioned above.

The present invention is further in clear distinction to the technology described in WO 2006/102347, which neither discloses crystalline nanostructures to be formed nor that yttrium-stabilized zirconia is used as nanostructuring material.

By the feature that the coating comprises crystalline nanostructures having at least approximately the shape of a regular convex polyhedron, the present invention is further in very clear contrast to the disclosure of U.S. Pat. No. 6,586,115, which relates to a thermal barrier coating, in particular for gas turbines, said coating consisting of zirconia partially stabilized with yttria and having a microstructure of columnar grains.

According to a further preferred embodiment of the present invention, the coating essentially consists of crystalline nanostructures, thus allowing for a uniform distribution of sites of improved protein adherence.

With regard to the crystallographic structure, the nanostructures preferably are of a cubic, cubic-like or tetragonal phase, and in particular are of an intermediate phase between a tetragonal and a cubic phase, as mentioned above, since for these a specifically high biological activity has been determined.

According to a further preferred embodiment, the nanostructures or the portion thereof being defined by the crystal habitus according to the present invention have a size of less than 200 nm, preferably less than 100 nm, more preferably less than 50 nm, and most preferably a size ranging from 1 to 30 nm. In this context, the size relates to the maximum extent of the nanostructures or the nanostructure portion in two dimensions and can in particular be determined by Field Emission Scanning Electron Microscopy (FESEM), which is well-known to the skilled person. Specifically, the sizes mentioned above relate to the maximum extent of the regular convex polyhedron defining the crystal habitus of the nanostructures or the nanostructure portion.

Preferably, the surface of the dental article body, on which the coating is formed, is rough, and more preferably has a roughness in a macroscopic and/or microscopic scale. Most preferably, it has a roughness obtainable by sand-blasting and acid etching, i.e. a macroroughness superimposed by a microroughness, as e.g. obtainable by the treatment described in EP-A-1 982 670.

It has been found that the retentive component of a surface comprising a macroroughness and a microroughness superimposed thereon is not affected by adding the nanostructures according to the present invention, but that the nanostructures add an improved biological activity to the surface, ultimately leading to optimum osseointegration. In addition, the previously reported problems of yttrium depletion caused by etching the surface can be circumvented, as mentioned above.

By choosing a thickness of the coating of about 100 nm at most, preferably of about 70 nm at most, and most preferably of about 50 nm at most, the macroscopic and/or microscopic roughness as obtained by the sandblasting and/or etching procedure, for example, is not "buried" under the coating, but still displays its beneficial properties regarding tissue interaction. Thus, the surface topography obtained by the pre-treatment retains its osseointegrative properties, which by adding the nanostructures of the present invention is optimized further, rather than being deteriorated.

According to a further aspect, the present invention also relates to a process for providing a dental article as described above, the process comprising the steps of
a) providing a dental article body made of ceramic material, and
b) forming on the surface of the dental article body a coating comprising crystalline nanostructures made of yttria-stabilized zirconia $YSZ_1$ by physical vapor deposition using a target made of a zirconium-yttrium alloy.

According to a further preferred embodiment, the coating is formed by sputter deposition.

As mentioned above, a surface of improved biological activity can be achieved by this process. At the same time, by the addition of yttrium (in the form of $YSZ_1$) a replenishment of yttrium in yttrium depletion zones can be achieved, which may occur during pre-treating the body by acid etching.

Given that by the coating formed in step b) a nanoscopic roughness is formed, which enhances the biological activity of the surface, the process is thus completely different to previously described sputtering processes as e.g. disclosed in WO 2012/030565, which aims at providing a smooth, low friction surface and which uses a ceramic target, rather than a target made of a zirconium-yttrium alloy. Thus, a metallic target is used according to the process of the present invention, in contrast to the use of a ceramic target taught in WO 2012/030565.

As will be discussed below, the oxygen required as reactive gas for forming yttria-stabilized zirconia from the metallic zirconium-yttrium target is typically provided by the gas used in the physical vapor deposition.

As an alternative to the above defined process using a zirconium-yttrium alloy, the present invention further relates to a process comprising step a) and b) defined above, but by using a zirconium target and an yttrium target instead of a target made of a zirconium-yttrium alloy. Hence, two targets are used according to this process, both of which are also metallic and are thus clearly different to the ceramic target used according to WO 2012/030565.

Specifically, the present invention therefore also relates to a process for providing a dental article as described above, the process comprising the steps of
a) providing a dental article body made of ceramic material, and
b) forming on the surface of the dental article body a coating comprising crystalline nanostructures made of yttria-stabilized zirconia $YSZ_1$ by physical vapor deposition using a target made of zirconium and a target made of yttrium.

As mentioned, the thickness of the coating applied preferably is about 100 nm at most, preferably of about 70 nm at most, and most preferably of about 50 nm at most. The process according to this specific embodiment is thus even further remote from known sputtering processes for providing a thermal barrier coating on gas turbines, which aim at a much higher coating thickness.

Typically, an oxygen containing gas is used for the physical vapor deposition, in particular a gas containing between about 0.5 to 2 vol-%, more particularly about 0.5 to 1.5 vol-% oxygen. Specifically, the gas flow for an embodiment defined by these oxygen ranges can be at 40 sccm O2 and 3500 sccm Ar.

According to a particularly preferred embodiment, the coating is formed by gas flow sputter deposition. Specifically, the gas flow sputter deposition performed makes use of a hollow cathode plasma source, whereby some regions of the hollow cathode contribute to the plasma generation (active areas) and other regions that are not used for plasma generation (passive areas) are screened by methods known to the person skilled in the art. For a detailed description of the technology, it is hereby referred to EP-A-2 367 196, the content of which, and in particular of paragraphs [0020] to [0058], is incorporated herewith by reference.

Gas flow sputter deposition has been found to be particularly preferred, since it allows to avoid target poisoning, in particular oxidation of the target, by separating the metal source from the oxygen source. In addition, the nanostructures formed by gas flow sputter deposition are of relatively low energy, which supports an undisturbed crystalline growth.

If the dental article body to be coated is a dental implant or a dental implant abutment, the body is preferably rotated during sputter deposition, thus constantly changing its orientation in relation to the sputter source.

According to a further preferred embodiment of the process, the physical vapor deposition is performed at a temperature above room temperature, preferably a temperature of at least 80° C., more preferably in a temperature range from 200° C. to 500° C., and most preferably from 300° C. to 450° C.

Typically, the process time of the physical vapor deposition, and specifically the gas flow sputter deposition, is set within a range from about 10 to 120 seconds, preferably from about 30 to 60 seconds. The substrate distance is set in a range from 30 to 150 mm, preferably from 60 to 120 mm, and most preferably at about 100 mm.

As mentioned above, the dental article body, on which the coating is formed, is preferably rough, and particularly has a roughness in a macroscopic and/or microscopic scale. According to a preferred embodiment of the process, the surface of the basic body is therefore roughened prior to the physical vapor deposition, in particular by sand-blasting and/or acid etching. Regarding the etching, an etching medium containing hydrofluoric acid can be used. If by the etching a depletion of yttrium is caused, yttrium is replenished by the coating formed according to the present invention comprising crystalline nanostructures made of yttria-stabilized zirconia, as discussed above.

As also mentioned above, the formation of the coating according to step b) can be carried in out in a manner, in which osseointegrative properties of the macroroughness and the microroughness previously provided to the body remain unaffected. In particular, the coating is formed such that the relevant surface topography parameters remain unchanged or are only changed to a minor degree.

As mentioned above, it is preferred that a macroscale roughness is formed by a sand-blasting step and a microscale roughness superimposing the microscale roughness is formed by a subsequent acid etching step. Preferably, the microscale topography formed can be defined by at least one of the surface parameters $S_a$, $S_t$ and $S_{sk}$:
i) $S_a$ being the arithmetic mean deviation of the surface in three dimensions and being preferably in the range from 0.1 μm to 2.0 μm, more preferably being in a range from 0.2 μm to 1.5 μm, even more preferably from 0.3 μm to 0.7 μm;
ii) $S_t$ being the maximum peak to valley height of the profile in three dimensions and being preferably in the range from 0.5 μm to 20.0 μm, more preferably being in a range from 1.0 μm to 15.0 μm, even more preferably from 2.0 μm to 9.0 μm; and/or
iii) $S_{sk}$ being the skewness of the profile in three dimensions and being preferably in the range from −0.01 to −0.6, more preferably from −0.05 to −0.4, and most preferably from −0.1 to −0.3.

The surface parameters are known to the skilled person and are analogue parameters for three dimensions to the parameters $R_a$, $R_t$ and $R_{sk}$, respectively, defined in EN ISO 4287 for two dimensions. Specifically, the above values relate to the values as obtainable by optical methods, and more specifically as obtainable by the software Mountains-Map by Digital Surf known to the skilled person.

The above values for $S_a$, $S_t$ and $S_{sk}$ relate in particular to a bone contacting surface of the body, i.e. a surface area located such on the body, specifically the implant, to come into contact with bone tissue after implantation. For a soft tissue contacting surface of the body, the preferred values are smaller.

According to a particularly preferred embodiment of the invention, step b) of the process is carried out in a manner that by the coating at least one of $S_a$, $S_t$ and $S_{sk}$ is changed by less than 50% at most, preferably by 30% at most, more preferably by 20% at most and most preferably is kept essentially unchanged.

EXAMPLES

The present invention is further illustrated by way of the following examples together with the attached figures.

Sample disks of yttria-stabilized zirconia (Y-TZP, MZ111 hipped by CeramTec GmbH) having a diameter of 6.25 mm and a height of 3 mm were sand-blasted using corundum of a grain size in the range from 0.12 to 0.25 mm and at a blasting pressure of 1.5 bar. The sandblasted samples were then acid etched using hydrofluoric acid (40%) at 95° C. for 10 minutes.

Of the samples obtained by the above procedures ("ZLA samples"), one part was then subjected to gas flow sputter deposition using a target made of a zirconium-yttrium alloy, while the other remained untreated. Specifically, an alloy having a stoichiometry of 8Y-PSZ, more specifically Y16Zr84, was used as target.

Specifically, the gas flow sputter deposition was carried out at a process temperature of 400° C. for 36 seconds. The flow of the reactive gas was set to 40 sccm, with the process pressure being at 0.2 mbar and the substrate-target distance being 100 mm. 6 cycles have been carried out.

By this process, coating a comprising crystalline nano-structures made of yttria-stabilized zirconia $YSZ_1$ containing 8 mol-% of yttria is achieved.

For a further set of samples ("double-blasted ZLA masking"), the same treatment as for the "ZLA masking" samples was performed with the difference that two sandblasting steps were carried out instead of one, namely a first sand-blasting step using corundum of a grain size in the range from 0.12 to 0.25 mm (at a blasting pressure of 1.5 bar) and a second sandblasting step using corundum of a grain size in the range from 0.045 to 0.075 mm (at a blasting pressure of 1.5 bar).

The coated samples ("ZLA masking" and "double-blasted ZLA masking") were then sterilized using $H_2O_2$ and analysis of the surface was carried out as outlined in the following:

Surface Analysis

For each analysis method, three samples were analysed. Identical samples were used for the contact angle measurement, roughness measurement and FESEM measurement in the written order, whereas three different samples were analysed for their chemical composition by XPS.

Contact Angle

The contact angle measurements were performed using a sessile drop test with ultrapure water (EasyDrop DSA20E, Krüss GmbH). The droplet size for the contact angle measurements was set to 0.1 µl. Contact angles were calculated by fitting a circular segment function to the contour of the droplet placed on the surface (circle fitting procedure).

Chemical Composition

The chemical composition of the sample surface (outermost 5-10 nm) was determined by XPS. Spectra were acquired on a PHI5000 VersaProbe spectrometer (ULVAC-PHI, INC.) equipped with a focused scanning monochromatic Al-Kα source (1486.6 eV). The photoelectrons were detected at an angle of 45° to the surface normal. The measurements were performed with a spot size of 0.2 mm.

Roughness

The roughness images were acquired with a confocal microscope (usurf explorer, NanoFocus AG). Three discs were investigated and three measurements per discs were performed.

The following microscope/light parameters were used for the acquisition of the 3D roughness images:

20× objective (working distance 3.1 mm, n.a. 0.45), field of view 798 µm×798 µm, lateral resolution 1.56 µm, piezo-electric scanner, step size 0.22 µm, algorithm=fast, brightness 70%, camera settings: exposure time 38 ms, gain 1.5 dB.

The whole roughness image with a size of 798 µm×798 µm was used for the calculation of the 3D roughness parameters. The micro roughness (roughness) and macro roughness (waviness) values were determined using a moving average Gaussian filter with a cut-off wavelength of 31 µm.

Specifically, the arithmetic mean deviation ($S_a$; expressing as an absolute value the difference in height of each point compared to the arithmetical mean of the surface), the maximum peak to valley height ($S_t$) and the skewness ($S_{sk}$) were determined.

FESEM

The surface topography of each surface modification was characterized by means of FESEM (field emission scanning electron microscopy) measurements (Hitachi S-4800). High resolution images were acquired using the in-lens detector and an acceleration voltage of 5 kV.

Results of Surface Analysis

The results of the contact angle measurement for the ZLA and the ZLA Masking samples is presented in Table 1, evidencing a high hydrophilicity of the ZLA Masking samples with contact angles of around 10° or lower.

TABLE 1

Results of the contact angle (C.A. ) measurements (SD: standard deviation)

| Sample | Sample 1 C.A. [°] | Sample 2 C.A. [°] | Sample 3 C.A. [°] | Mean C.A. [°] | SD C.A. [°] |
|---|---|---|---|---|---|
| ZLA | 8.4 | 52.0 | 10.4 | 23.6 | 24.6 |
| ZLA Masking | 4.7 | 6.6 | 0.0 | 3.8 | 3.4 |

The chemical composition of the different samples as determined by XPS is shown in Table 2.

TABLE 2

Apparent normalized atomic concentration [%] (sum equals 100%) of the elements detected by XPS

| Sample | Zr [%] | Y [%] | C [%] | O [%] | N [%] | Si [%] | Na [%] | Al [%] | F [%] |
|---|---|---|---|---|---|---|---|---|---|
| ZLA | 27.3 | 1.3 | 18.0 | 48.1 | 0.3 | 0.0 | 0.6 | 0.0 | 4.4 |
| ZLA Masking | 22.7 | 3.9 | 23.3 | 48.2 | 0.0 | 0.0 | 0.0 | 0.0 | 2.0 |

As shown in Table 2, the surface composition consists mainly of Zr, Y, O and C due to the base material (Y-TZP) and a carbon containing contamination layer. Besides these elements some of the samples contain significant amounts of Al, Na and F and some trace amounts of N or Si (around 1% or lower).

Using the XPS results on Y and Zr contents, the yttria content was calculated according to the equation $$Y_2O_3(mol\ \%) = Y/2/(Zr+Y/2)*100$$

For the ZLA Masking samples, the calculation revealed clearly higher amounts of Y on the surface with values of about 8 mol % $Y_2O_3$ compared to the 2.4 mol % calculated for the ZLA samples.

The microscale roughness of the samples tested is shown in Table 3, whereas the macroscale roughness is shown in Table 4.

TABLE 3

| | Micro roughness. Mean values ± SD (standard deviation) | | | | | |
|---|---|---|---|---|---|---|
| Sample | $S_a$ [μm] | SD $S_a$ [μm] | $S_t$ [μm] | SD $S_t$ [μm] | $S_{sk}$ | SD $S_{sk}$ |
| ZLA | 0.640 | 0.029 | 3.89 | 0.15 | −0.113 | 0.055 |
| ZLA Masking | 0.610 | 0.031 | 3.74 | 0.19 | −0.143 | 0.016 |

TABLE 4

| | Macroscale roughness. Mean values ± SD (standard deviation) | | | | | |
|---|---|---|---|---|---|---|
| Sample | $S_a$ [μm] | SD $S_a$ [μm] | $S_t$ [μm] | SD $S_t$ [μm] | $S_{sk}$ | SD $S_{sk}$ |
| ZLA | 0.891 | 0.047 | 5.65 | 0.41 | −0.528 | 0.078 |
| ZLA Masking | 0.856 | 0.063 | 5.28 | 0.43 | −0.502 | 0.081 |

As shown in Tables 3 and 4, similar roughness values were obtained for ZLA and for ZLA Masking. Thus, the process of the present invention does not lead to characteristically different roughness values, but only adds a nanostructure (or sub-micrometer structure) superimposing the macroscale and the microscale structure. In particular, the macroscale and the microscale roughness remain unchanged in view of their $S_a$, $S_t$ and $S_{sk}$ values.

Images of the respective surfaces are shown in the attached figures of which

Figure 1:
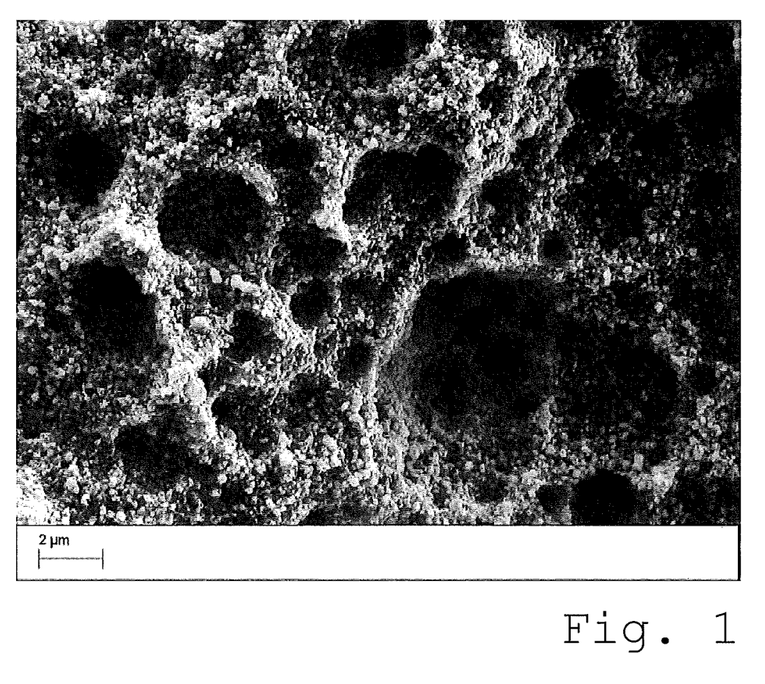
FIG. 1 shows a FESEM image of the "ZLA" sample (comparative) at a nominal magnification of 5000× with the scale representing 2 μm given in the lower left corner of the image.
Figure 2:
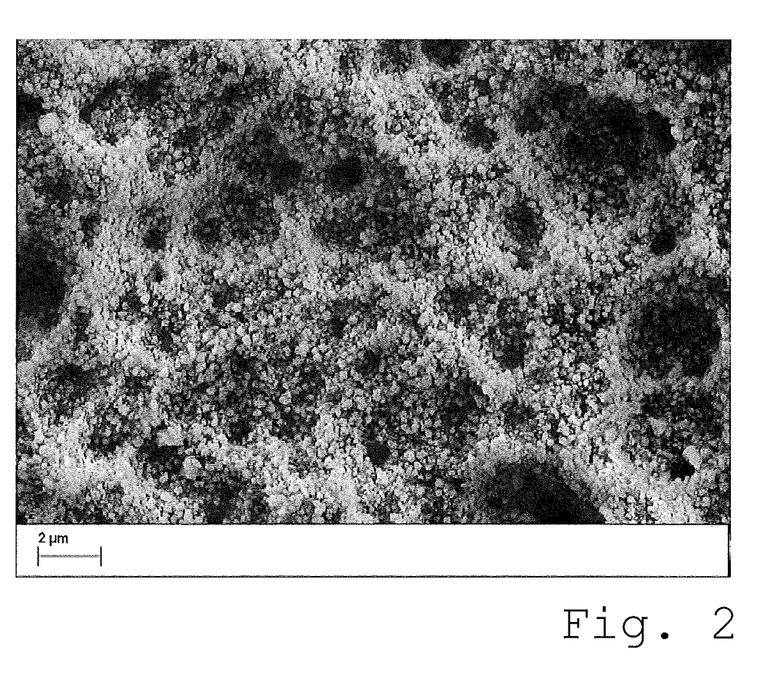
FIG. 2 shows a FESEM image of the "ZLA masking" sample (according to the invention) at a nominal magnification of 5000× with the scale representing 2 μm given in the lower left corner of the image.
Figure 3:
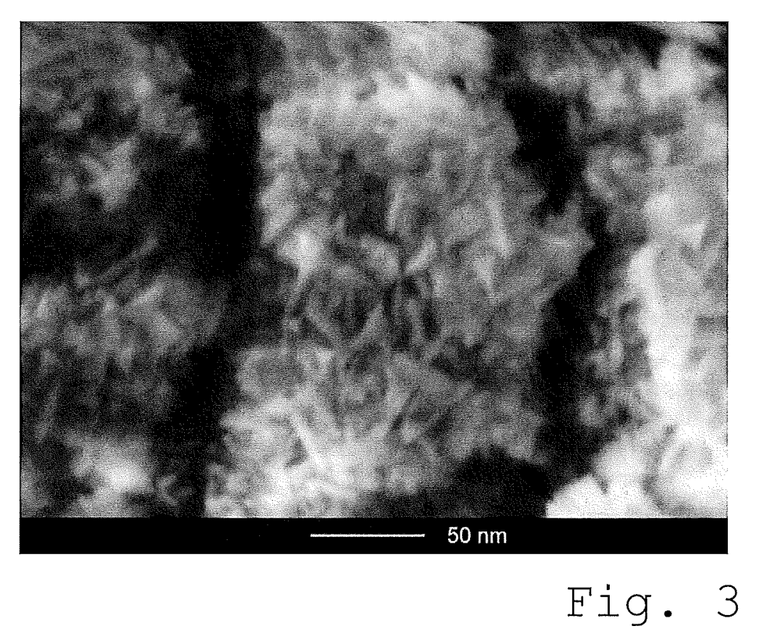
FIG. 3 shows a high resolution FESEM image of the "ZLA masking" sample (according to the invention) with the scale representing 50 nm given at the bottom of the image.
Figure 4:
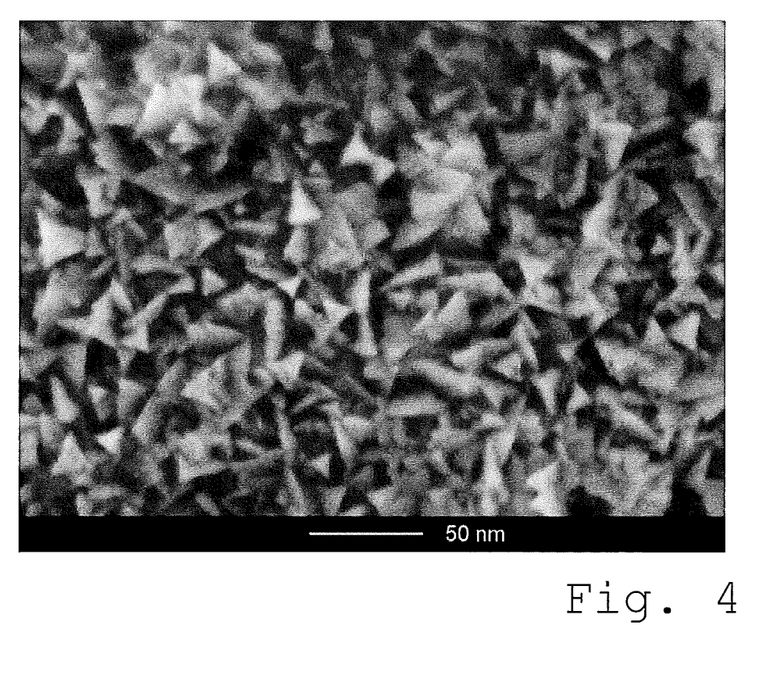
FIG. 4 shows a high: resolution FESEM image of the "double-blasted ZLA masking" sample (according to the invention) with the scale representing 50 nm given at the bottom of the image.

As in particular shown in FIGS. 3 and 4, nanostructures having the crystal habitus of a tetrahedron are achieved by the process of the present invention.

Figure 5:
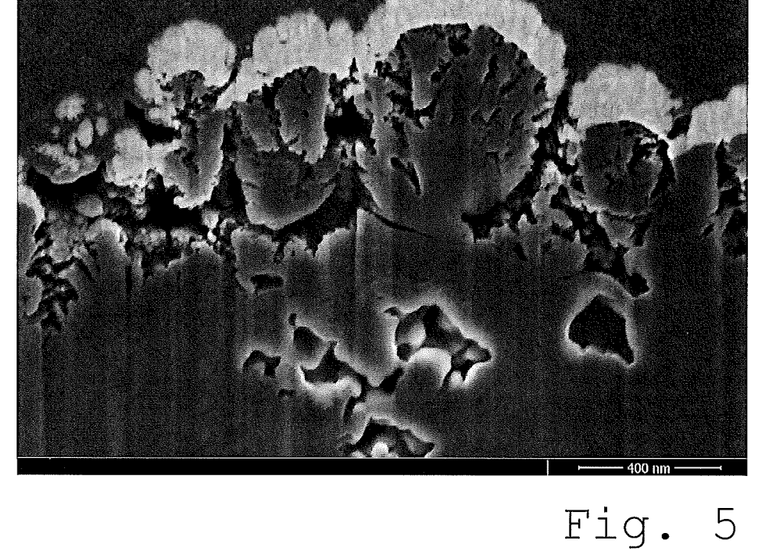
FIG. 5 shows a sectional image of a sample obtained by gas flow sputter deposition as specified above, but using 20 (instead of 6) deposition cycles, with the scale representing 400 nm given at the bottom of the image.
Figure 6:
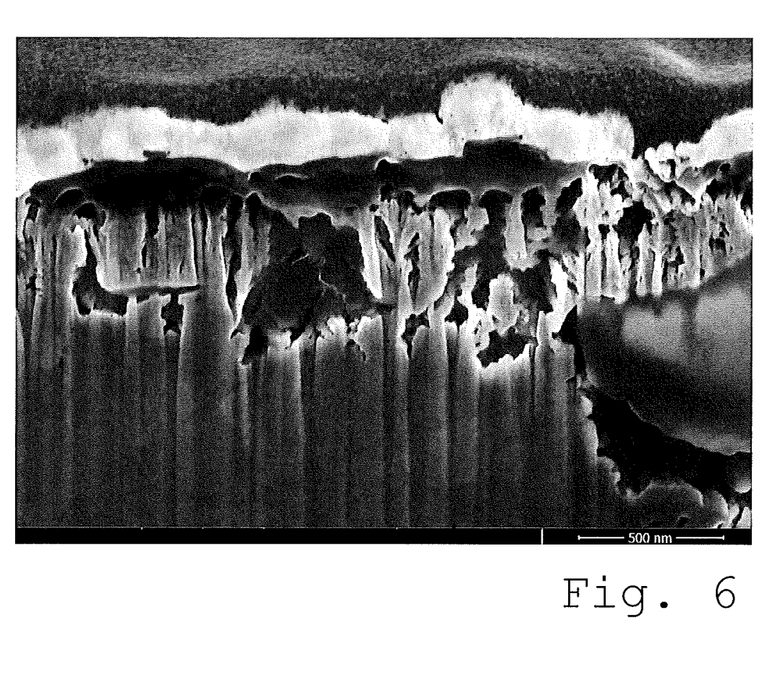
FIG. 6 shows a sectional image of a sample obtained by gas flow sputter deposition as specified above, but using a flow of the reactive gas of 60 sccm (instead of 40 sccm), with the scale representing 500 nm given at the bottom of the image.

As shown in FIGS. 5 and 6, the nanostructures obtained have on their distal side the shape of the respective sector of a regular convex polyhedron, while having at their proximal side a columnar shape forming a surface oriented tilted columnar structure, which is a result of the nanostructures being conjoined with the surface of the dental article body. In a sectional view, these nanostructures can be described as having the shape of a cauliflower, the stem of which being formed by the columnar portion and the florets by the sector of the regular convex polyhedron.

As also shown in FIGS. 5 and 6, there is no interface between the columnar portion and the substrate, i.e. the dental article body. Rather, the nanostructures protrude from the substrate as a continuous material formation. (The light areas in the images according to FIGS. 5 and 6 relate to a Pt layer deposited for the protection of the nanostructures against the Ga-ion beam of the FIB.)

The biological activity of ZLA and ZLA masking samples has been assessed by a-biological pull-off tests ("a-bio") using a dental plastic (Exakto-Form Modellkunststoff, bredent GmbH & Co. KG). Specifically, sample disks of a diameter of 15 mm and a height of 1 mm or 1.5 mm were analysed for their pull-off force at a pull-off speed of 0.83 mm/s. These a-bio pull-off forces were compared to the respective pull-off force determined for the sample in vivo.

The results are shown in Table 5.

TABLE 5

| | Pull-off tests (a-biological and in vivo) | | | |
|---|---|---|---|---|
| | ZLA | | ZLA Masking | |
| | a-bio | in vivo | a-bio | in vivo |
| Average (N) | 179 | 30 | 171 | 45 |
| STD (N) | 107 | 13 | 83 | 16 |
| a-bio/in vivo | | 6 | | 4 |

According to Table 5, the ZLA Masking sample showed a markedly higher pull-off force in vivo compared to the ZLA sample. Dividing the pull-off force (a-bio) by the pull-off force (in vivo) results for the ZLA Masking sample in a relatively small value of less than 4. Since a small value is indicative of a high biological activity, the results indicate that the process of the present invention leads to an improved biological activity (compared to the untreated sample for which the above division results in a much higher value of about 6).

The invention claimed is:

1. A dental article comprising a dental article body made of a ceramic material and crystalline nanostructures formed on the surface of the dental article body, the crystalline nanostructures forming nanoscopic peaks projecting outward from the surface of the dental article body, wherein the crystalline nanostructures are made of yttria-stabilized zirconia $YSZ_1$, the crystal habitus of at least a portion of the nanostructures having at least approximately the shape of a regular convex polyhedron.

2. The dental article according to claim 1, wherein the crystal habitus of at least a portion of the nanostructures has at least approximately the shape of a tetrahedron or an octahedron.

3. The dental article according to claim 1, wherein the nanostructures have a cubic crystallographic structure, a tetragonal crystallographic structure, or a crystallographic structure in an intermediate phase between a tetragonal and a cubic phase.

4. The dental article according to claim 1, wherein the amount of yttria in the yttria-stabilized zirconia $YSZ_1$ is higher than 3 mol-%.

5. The dental article according to claim 1, wherein the amount of yttria in the yttria-stabilized zirconia $YSZ_1$ is lower than 12 mol-%.

6. The dental article according to claim 1, wherein the amount of yttria in the yttria-stabilized zirconia $YSZ_1$ is in a range from 6 to 8 mol-%.

7. The dental article according to claim 1, wherein the nanostructures have a size of less than 200 nm.

8. The dental article according to claim 1, wherein the dental article body is made of zirconia.

9. The dental article according to claim 8, wherein
the dental article body is made of yttria-stabilized zirconia $YSZ_2$, and
the percentage of yttrium in the yttria-stabilized zirconia $YSZ_1$ differs from the percentage of yttrium in the yttria-stabilized zirconia $YSZ_2$.

10. The dental article according to claim 1, wherein the surface of the dental article body, on which the crystalline nanostructures are formed, is rough.

11. The dental article according to claim 1, wherein the crystalline nanostructures have a thickness of 100 nm at most.

12. A dental implant comprising the dental article according to claim 1.

13. The dental article according to claim 1, wherein the crystalline nanostructures form a nanoscopic roughness on the surface of the dental article body.

14. A process for providing the dental article according to claim 1, the process comprising
   a. providing the dental article body made of the ceramic material, and
   b. forming on the surface of the dental article body the crystalline nanostructures made of yttria-stabilized zirconia $YSZ_1$ by physical vapor deposition using a target made of a zirconium-yttrium alloy or using a target made of zirconium and a target made of yttrium.

15. The process according to claim 14, wherein the crystalline nanostructures are formed by sputter deposition.

16. The process according to claim 14, wherein an oxygen containing gas is used for the physical vapor deposition, a gas containing between 0.5 to 2 vol-% oxygen.

17. The process according to claim 14, wherein the physical vapor deposition is performed at a temperature above room temperature.

18. The process according to claim 14, wherein prior to the physical vapor deposition, the surface of the dental article body is roughened.

19. The process according to claim 18, wherein a microscale roughness is formed on the dental article body prior to step b, the microscale roughness being defined by at least one of surface parameters $S_a$, $S_t$ and $S_{sk}$:
   i. $S_a$ being the arithmetic mean deviation of the surface in three dimensions and being in the range from 0.1 μm to 2.0 μm;
   ii. $S_t$ being the maximum peak to valley height of a profile in three dimensions and being in the range from 0.5 μm to 20.0 μm; and
   iii. $S_{sk}$ being the skewness of the profile in three dimensions and being in the range from −0.01 to −0.6, and
by the crystalline nanostructures formed in step b, at least one of $S_a$, $S_t$ and $S_{sk}$ is changed by less than 50% at most.

* * * * *